(12) United States Patent
Lu et al.

(10) Patent No.: US 8,999,712 B1
(45) Date of Patent: Apr. 7, 2015

(54) ASSAY FOR PLANT ROOT PATHOGEN ACTIVITY

(75) Inventors: Guihua Lu, Beijing (CN); Julie Qi, Urbandale, IA (US); Jennifer S. Tallman, Des Moines, IA (US); Xu Hu, Johnston, IA (US); Yaxin Li, Johnston, IA (US)

(73) Assignee: Pioneer Hi-Bred International Inc., Johnston, IA (US)

( * ) Notice: Subject to any disclaimer, the term of this patent is extended or adjusted under 35 U.S.C. 154(b) by 251 days.

(21) Appl. No.: 12/942,549

(22) Filed: Nov. 9, 2010

Related U.S. Application Data (60) Provisional application No. 61/259,393, filed on Nov. 9, 2009.

(51) Int. Cl.
| | |
|---|---|
| *C12N 5/00* | (2006.01) |
| *C12N 5/02* | (2006.01) |
| *A01G 31/00* | (2006.01) |
| *A01G 9/00* | (2006.01) |
| *A01G 13/02* | (2006.01) |
| *C12Q 1/02* | (2006.01) |

(52) U.S. Cl.
CPC ...................................... *C12Q 1/025* (2013.01)

(58) Field of Classification Search
CPC ............... A01N 2300/00; A01N 43/22; C12N 15/8285; C12N 15/8286; C12N 15/8282; A01H 1/04
USPC ............. 435/431, 426, 420, 410; 47/58.1 SC, 47/59 S, 32.8; 800/312; 504/367
See application file for complete search history.

(56) References Cited

U.S. PATENT DOCUMENTS 5,972,689 A * 10/1999 Cook et al. ............... 435/252.31
7,123,750 B2 10/2006 Lu et al.

OTHER PUBLICATIONS

Shepherd. 1979. Phytopathology 69(4): 427-430.*
Narayanan et al., Expression of Soybean Cyst Nematode Resisance in Transgenic Hairy Roots of Soybean, Crop Science, vol. 39, No. 6, p. 1680-1686.*
Ownley et al., Phytopathology 82:178-184, 1992.*
Cho, H-J., et al., "High-Efficiency Induction of Soybean Hairy Roots and Propagation of the Soybean Cyst Nematode," *Planta*, 2000, pp. 195-204, vol. 210.
Narayanan, R.A., el al., "Cell Biology & Molecular Genetics: Expression of Soybean Cyst Nematode Resistance in Transgenic Hairy Roots of Soybean," *Crop Sci.*, 1999, pp. 1680-1686, vol. 39.
Niblack, T.L., el al., "A Standard Greenhouse Method for Assessing Soybean Cyst Nematode Resistance in Soybean: SCEo8 (Standardized Cyst Evaluation 2008)," *Plant Health Progress*, May 13, 2009, on-line publication.
Plovie, E., et al., "Hairy Roots to Test for Transgenic Nematode Resistance: Think Twice," *Nematology*, 2003, pp. 831-841, vol. 5(6).
Lu, H., et al., "An Innovative Method for Counting Females of Soybean Cyst Nematode with Fluorescence Imaging Technology," *Journal of Nematology*, 2005, pp. 495-499, vol. 37(4).

* cited by examiner

*Primary Examiner* — Anne Grunberg
(74) *Attorney, Agent, or Firm* — Pioneer Hi-Bred Int'l Inc.

(57) ABSTRACT

A method for improving the sensitivity of an assay to determine the pathogenicity of a plant root pathogen using a soil amendment is presented. The method involves growing the plant root in the presence of a soil amendment after exposure of the plant root to the pathogen. A method of breeding plants is also provided.

9 Claims, 4 Drawing Sheets

Effect of Turface on Assay Sensitivity

Figure 3

Turface with Varying Moisture Levels

Figure 4

ASSAY FOR PLANT ROOT PATHOGEN ACTIVITY

CROSS-REFERENCE TO RELATED APPLICATIONS

This application claims the benefit of U.S. Provisional Application No. 61/259,393, filed Nov. 9, 2009, which is hereby incorporated herein in its entirety by reference.

FIELD OF THE INVENTION

The present invention relates to methods of evaluating the pathogenicity of a plant root pathogen and, more particularly, to methods for increasing the sensitivity of an assay for evaluating the pathogenicity of plant root pathogen.

BACKGROUND

Plant pathogens cause considerable damage to agricultural plants every year. In soybeans alone it is estimated that plant pathogens account for, on average, a reduced yield of over 400 million bushels per year. Plant root pathogens typically account for over 40% of that loss (nearly 170 million bushels per year). Nearly all plants are susceptible to root pathogens and suffer damage resulting in yield loss from these pathogens.

One example of a plant root pathogen which causes significant crop damage is soybean cyst nematode (SCN), *Heterodera glycines*. SCN is a small plant-parasitic roundworm which preferentially attacks soybeans. SCN has been known to cause significant damage to soybean fields and is responsible for, on average, over 150 million bushels worth of damage to soy crops.

The second stage juvenile of SCN is the only stage which is able to penetrate roots. After entering the root, the SCN moves to the vascular tissue where it begins to feed. SCN is able to induce cell division in the root which results in the formation of feeding sites for the growing SCN. Feeding females remain stationary and continue to feed. Eventually, the female becomes large enough to break through the root tissue such that they are exposed on the surface of the root.

Males remain mobile and fertilize the exposed females who begin to produce eggs. Initially eggs are contained in an egg sac outside the female's body, however, eventually the entire body of the female becomes filled with eggs and the female dies. The egg filled body of the female is called a "cyst."

The cysts eventually dislodge from the plant and remain in the soil. The walls of the cyst provide protection for approximately 200-400 eggs stored inside. The eggs may remain in the soil for up to several years, waiting for appropriate hatching conditions.

The symptoms of SCN infection frequently appear as an oval of plant damage, elongated in the direction of tillage, with relatively sharply defined borders. The damaged plants typically are late to close in with foliage and show stunted growth and yellowing of the plants. The effects of SCN vary greatly based on soil type, plant variety, and environmental conditions. Frequently plants in light sandy soils exhibit more extensive injury than plants in heavier soils.

Another example of a plant root pathogen is the root knot nematode. Root knot nematodes belong to the genus *Meloidogyne*. Although there are many species of root knot nematodes, the four most common species are *M. incognita, M. hapla, M. javanica*, and *M. arenaria*. Approximately 2000 types of plants, including tomato, soy, and maize, may be infected by some form of root knot nematodes. Infection by root knot nematode has been estimated to cause up to 5% of global crop loss.

When soil conditions are favorable (generally greater than 50° F.) and host plants are being grown, the root knot nematode will begin to grow. After reaching the second stage juvenile phase, the nematodes will hatch from their eggs and move through the soil to find plant roots. Upon reaching a root, the nematode penetrates the root and begins feeding.

The nematode causes the cells in the plant parenchyma to become multi-nucleate. These cells become "giant cells" which the nematode uses as a feeding site. The site also turns into a gall, which is a protrusion of the root in which the nematode develops.

After several molts the female is ready to begin laying eggs. The female deposits eggs in a gelatinous matrix which serves to protect the eggs. Eventually, the egg masses dissociate from the plant and remain in the soil. The eggs then begin development once conditions are favorable for hatching.

A number of techniques are being pursued in order to limit the damage by plant pathogens in general and plant root pathogens in particular. Approaches include rotating crops, the use of pesticides, and increasing plant resistance through traditional breeding and genetic manipulation.

In order to effectively use these techniques, researchers must have the ability to determine the pathogen's ability to survive and thrive on the plant. This measure of the pathogen's ability to survive on plant tissue is referred to as the pathogenicity of the pathogen. Using an accurate and sensitive measure of pathogenicity, researchers can then effectively compare the resistance of different plants, the pathogenicity of various pathogens, and select plants for breeding or manipulation to increase plant resistance.

One example of an assay of plant damage is the hairy root assay. In this assay, transgenic roots are created which have fine fibrous roots. This type of root can be generated through the use of a number of plant pathogens including *Agrobactreium rhizogenes* and *Agrobacterium tumefaciens*. The hairy roots are then subjected to a plant pathogen of interest and pathogenicity is measured. Various measures of pathogenicity exist including counting the number of parasites which survive exposure and direct assays of root damage (e.g. root weight).

A significant problem with the current assay technique is that the measures of pathogenicity are so low that background noise can sometimes drown out a treatment effect. As a result, researchers are left with using ever higher numbers of replicates to decrease the noise or face the real possibility of going forward with ambiguous results. (Plovie, et. al., Nematology, 2003, Vol. 5(6), 831-841)

Thus there exists a need in the art for increasing the sensitivity of assays for pathogenicity.

BRIEF SUMMARY OF THE INVENTION

The invention provides methods for increasing the sensitivity of assays of pathogenicity. In the improved assay of the invention, the plant roots are grown in the presence of a soil amendment which results in increased plant root pathogen pathogenicity. This increase in pathogenicity raises the average scores of plant damage for increased pathogenicity conditions (e.g. susceptible plants, resistant pathogens, negative controls). The increased score allows the increased pathogenicity conditions to be more accurately distinguished from background.

In one embodiment of the invention plant roots are exposed to a pathogen of interest, the plant roots are then allowed to grow on a root culturing substrate in the presence of a soil amendment. After the plants have been allowed to grow for a period of time, the pathogenicity is measured. The measure of pathogenicity may be a measure of damage to the plant (e.g. dry root mass) or a measure of the plant pathogen's success (e.g. number of visible plant pathogens). This measure of pathogenicity may then be used to determine the plant's resistance to the pathogen, the pathogenicity of the pathogen, or the score may be used as part of a breeding program.

DETAILED DESCRIPTION

The present invention may be used to improve the sensitivity of any assay regarding the pathogenicity of plant root pathogens. In one method of the present invention a plant root is exposed to a plant pathogen of interest, after the exposure the plant is grown on a root culturing media in the presence of a soil amendment. After a suitable time, a measure of pathogenicity is taken. The soil amendment increases the infection rate of the pathogen increasing the sensitivity of the bioassay.

The methods of the present invention may be used on any plant to evaluate the pathogenicity of any plant root pathogen. Specifically, the methods may be used on monocots and dicots. Examples of appropriate plants include maize, wheat, rice, millet, barley, sorghum, rye, alfalfa, oilseed *Brassica*, cotton, soybean, sunflower, potato, or tomato. The methods may also be used for any plant root pathogen including nematodes. Examples of nematodes which may be used in the present invention include soybean cyst nematode and root knot nematode.

There are a number of assays where sensitivity may be improved by the methods of the invention. One example is the hairy root assay which is used to assay the pathogenicity of various plant root parasites. The hairy root assay is a faster alternative to greenhouse testing for transgenic plants. For an overview of the greenhouse method see T. Niblack et al., *A Standard Greenhouse Method for Assessing Soybean Cyst Nematode Resistance in Soybean: SCE08*, Plant Health Progress, May 13, 2009 which is hereby incorporated by reference in its entirety. In the case of soybeans, the generation of transgenic plants for a greenhouse assay will generally take two years. Appropriate transgenic material for the hairy root assay can be produced in as little as one month. As a result, use of the hairy root assay can drastically reduce the time required to produce pathogenicity data.

In the hairy root assay, plant tissue is grown on callus inducing media. The plant tissue is transformed with *Agrobacterium* and then cultured on regular culture medium. Eventually hairy roots begin to form which can be subcultured on regular culture medium. Typically, the plant tissue is transformed with T-DNA from a *A. rhizogenes* root-inducing (Ri) plasmid.

The subcultured roots are exposed to the plant pathogen and the infested roots are allowed to grow. After a suitable time, the pathogenicity of the plant pathogen is measured. Typically, this measure consists of a count of the parasite number. In the case of SCN, the number of cysts may be counted as an objective measure of pathogenicity. Alternatively, other measures such as root area and root dry weight may be measured to determine the extent of the damage caused by the pathogen.

Despite the considerable time savings of using the hairy root assay, the assay suffers from a small effect size. In a typical study the use of a susceptible plant/pathogen combination can result in average counts of nematodes between 3 and 13, the addition of a resistance trait yields results between 0 and 11. (Plovie, et. al., Nematology, 2003, Vol. 5(6), 831-841) As a result, the treatment group scores overlap considerably. In order to effectively discriminate between effects, a large number of replications is required and even then it can be difficult to discriminate a true result from background noise of the experiment.

An increase in the maximum number of pathogens (in the above example, number of nematodes) would result in the ability to have a larger effect size. This larger effect size then increases the statistical power of the assay and it becomes easier to discern a true experimental effect from background variability. When used with the hairy root assay the methods of the invention increase the total number of individuals counted such that there is a larger effect size. This larger effect size increases the statistical power of the assay producing more reliable results with lower replicates. This results in better results for lower cost in a shorter time.

In one method of the present invention, the hairy root assay is modified by growing the root of the plant in the presence of a soil amendment. For example, the soil amendment may be placed over top of the infested hairy roots as they are being grown. When this method is used for the hairy root assay to evaluate the pathogenicity of SCN on soybean, the addition of the soil amendment results in a statistically significant increase in the number of cysts found for susceptible plants.

In this manner, the addition of a soil amendment to nematode-infected plant roots growing on medium significantly increases the nematode infection rate. The enhanced infection rate significantly improves the sensitivity of the bioassay involving nematode resistance traits and genes. Thus, the methods can be used to select plants, particularly soybean plants, that show increased resistance to nematodes, particularly soybean cyst nematodes (SCN). The methods are also useful for screening candidate resistance genes for nematodes.

Growing SCN-infected roots in the presence of a soil amendment increases the SCN infection rate by at least about 70%, about 80%, about 90%, about 100%, about 110% or greater. Likewise, the use of a soil amendment increases the SCN infection rate in TO soybean plants by at least about 1-fold, about 1.5-fold, about 2-fold or higher.

In the hairy root SCN assay, the roots grown on a plate with a soil amendment have a well-distributed root system. Roots grown without a soil amendment have a more tangled and dense root structure which makes locating and counting the SCN cysts more difficult. The well-distributed root system resulting from the use of a soil amendment makes locating and counting SCN cysts significantly easier.

As noted, the roots are grown on a root culturing substrate. Root culturing substrates includes agar and other substrates for plant and root tissue culture. In the same manner, other ingredients used in tissue culture may be present.

Figure 1:
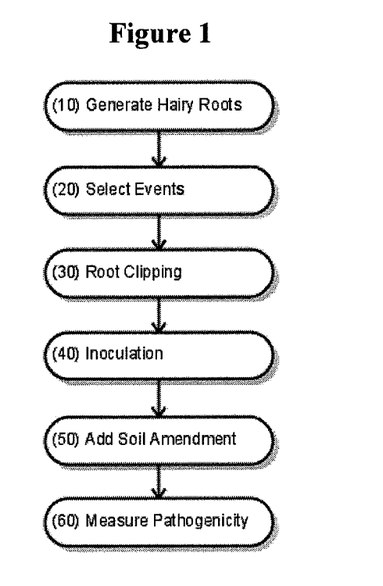
FIG. 1 is a diagram showing an improved hairy root assay for soybean cyst nematode performed in accordance with the methods of the present invention.

FIG. 1 provides a graphical depiction of one method of the present invention where the hairy root assay is adapted to accommodate the growth of the infected root in the presence of a soil amendment. As shown in FIG. 1, generation of hairy roots (10) is accomplished by growing plants transformed with *Agrobacterium* on a suitable root culturing substrate (e.g. soil, growth medium, etc.), event selection (20) is then performed on the hairy roots where suitably sized root portions are dissected out, selection of the appropriate roots can be assisted through the use of genes which make it easy to identify transformed root portions (e.g. reporter genes such a green fluorescent protein, selection genes such as resistance to antibiotics, etc.), the selected events are then clipped and grown on a suitable substrate (30) (such as growth medium), once the clipped roots are established they are inoculated (40) with the plant root pathogen of choice, after inoculation the plates are then grown in the presence of a soil amendment (50) (such as TURFACE® (calcined clay), sand, clay, cat litter, and others), after a suitable growth period (e.g. 7-8 weeks) the pathogenicity of the plant root pathogen is measured (60) (using a technique such as counting the number of pathogens present, measuring the plant dry root weight, and other measures of pathogenicity).

The methods of the present invention involve growing infected root tissue in the presence of a soil amendment. Soil amendments originated in sports field management. Persons responsible for the maintenance of athletic fields are faced with a unique challenge as athletic fields have areas of intense use. Despite this use, the fields need to maintain an aesthetically pleasing appearance. Additionally the fields need to be developed in a way to minimize athletic injuries which may result from dense and highly packed field conditions.

Typically, the preferred surface for an athletic field will provide cushioning for running and sliding and fielding balls, will not become slippery when wet, drains well and dries quickly (while retaining some moisture in extremely hot weather), and can be easily scarified through the use of an implement such as a nail drag to reduce surface compaction.

Because the wide variety of soil types used for various sport fields results in a wide variety of field conditions, a number of soil treatments have been developed to produce the desired qualities. These soil amendments help keep moisture levels relatively constant and avoid compaction.

These soil amendments have eventually come to be used in applications other than sports field maintenance. For example, soil amendments are now used in landscaping and agricultural uses. The use of soil amendments helps maintain appropriate soil moisture levels and provides better aeration of the soil which help promote overall plant health, particularly improved root health.

Examples of soil amendments include sand, cat litter, oil absorbents, grease absorbents, calcined diatomaceous earth, crushed aggregates, calcined clay, and combinations thereof. One form of calcined clay commonly used is smectite clay which may be beidellite, nontronite, hectorite, saponite, attapulgite, and sepiolite. The calcined clay may contain both montmorillinite and opal CT. Commercial examples of soil amendments include TURFACE® (calcined clay) produced by Profile Products, Mar-Co Clay Products, Diamond Pro, and Flex-a-clay by True Pitch.

The inventors have found that the addition of a soil amendment in pathogenicity assays results in an unexpected increase in the pathogenicity of plant root pathogens. As shown in the examples below the use of a soil amendment, such as TURFACE® (calcined clay), results in a significant increase in the score of pathogenicity. As stated above, the increased pathogenicity score increases the statistical power of the assay producing better results with reduced cost and effort.

In one method of the present invention, the roots are grown in the presence of a soil amendment after the roots have been exposed to a plant root pathogen of interest. Alternatively, the time in which the plant roots are grown in the presence of the soil amendment may be lengthened or shortened so long as at least a portion of the time occurs after exposure to the plant root pathogen of interest. Additionally, one or more changes of soil amendment may be employed, especially in experiments of longer duration.

In one method of the present invention, at least some portion of the plant root is in contact with the soil amendment. Preferably, at least some portion of the root is covered by the soil amendment. More preferably, a majority and/or all of the root is covered by the soil amendment.

Different results may be obtained by varying the amount of moisture added to the soil amendment. Preferably, the soil amendment has no water added to it before it is used in the assay. Alternatively, increasing amounts of water may be added to the soil amendment before use in the assay. Different amounts of water may be preferable for assays of different plant root pathogens. Techniques for determining the correct amount of water required for a particular pathogen are well within the level of skill in the art. An experiment which would allow one of skill in the art to select the appropriate moisture level is disclosed in Example 6 below.

Any number of methods may be used to measure the pathogenicity of the plant root pathogen used in the assay. In the event that individual pathogens leave an easily identifiable feature on the root (such as with SCN and root knot nematodes) the number of features may be tallied as a measure of pathogenicity. When the number of individuals can be counted, the number of individuals present on the root may be tallied. For pathogens that have multiple life stages, the number of individuals in a particular life stage may be tallied as a measure of pathogenicity.

Other measures are less dependent on the type of pathogen used in the assay. One example is dry root weight, which serves as a measure of pathogenicity by measuring direct root development. Alternatively, measures such as root area may be employed to determine pathogenicity. Generally, any method of measuring pathogenicity may be used with the method of the current invention.

The method of measuring may be manual or automated. For automated measurement, optical systems such as the one disclosed in U.S. Pat. No. 7,123,750 B2 (herein incorporated by reference in its entirety) may be used with the methods of the present invention.

Once a measure of pathogenicity has been obtained, a number of factors may be determined by the measurement. For example, the assay may be used to determine the effectiveness of pesticide resistance genes, pesticide treatments or pathogen resistance to such resistance genes and treatments.

In one method of the invention, the measure of pathogenicity demonstrates the effectiveness of a pesticide treatment. In such a method, at least two different treatment groups are used. Both treatment groups use the same type of pathogen and the same type of plant. One treatment group receives the pesticidal treatment (the experimental group) and another does not (the control group). The difference in pathogenicity between the experimental and control group is a measure of the effectiveness of the pesticidal treatment.

Alternatively, the same type of pathogen could be used across two treatment groups of plants. One group of plants could contain a resistance trait to the pathogen while the other could be a similar plant without the resistance trait. The difference in pathogenicity would reflect the effectiveness of the resistance trait. If the pathogen used was a pathogen which had developed tolerance to the resistance trait of interest, the difference in pathogenicity would reflect the level of pathogen tolerance to the resistance trait.

Alternatively, a tolerant and a susceptible group of pathogens may be used. The treatment groups may then be exposed to plants which show resistance to the pathogen. The difference in pathogenicity then reflects the level of tolerance exhibited by the tolerant pathogen. If non-resistant plants are used, then the difference in pathogenicity reflects the competitive burden placed on the tolerant pathogen in the absence of the plant's tolerance trait.

Examples of tolerant pathogens which may be used with the methods of the present invention include, but are not limited to, SCN race 3 on soybean Jack variety. Examples of pesticide treatments which may be used with the methods of the present invention include, but are not limited to, aldicarb (Temik). Examples of resistant plants which may be used with the methods of the present invention include, but are not limited to, SCN race 3 on Peking variety.

Of course, one skilled in the art can appreciate a wide variety of combinations regarding pathogens, treatments and plants which will measure other characteristics of interest to plant breeders and plant pathologists. Such combinations are within the scope and the spirit of the methods of the present invention.

The methods of the present invention may also be used as part of a plant breeding program. Pathogen resistant plants may be identified using the methods above. Plants exhibiting tolerance to a pathogen of interest may then be selected for further breeding to produce progeny plants with increased tolerance. This measure of increased tolerance may be determined by the methods of the present invention.

Optionally, the methods of the present invention may be used to identify plants which have been successfully genetically altered to exhibit tolerance to a pathogen of interest. Plants exhibiting tolerance may then be selectively bred with plants possessing other desirable qualities. The progeny plants resulting from such crosses may then be evaluated and selected for further breeding based, at least in part, on their ability to also tolerate the pathogen of interest. This measure of tolerance may be determined using the methods of the present invention.

The method additionally finds use in screening pathogen resistance genes, particularly SCN resistance genes. In this manner, transgenic plants comprising the gene or genes of interest can be tested according to methods of the invention. That is, constructs comprising a gene or genes of interest can be introduced into plant roots using *A. rhizogenes* according to the method of Plovie et al. (2003) *Nematology* 5(6):831-841, herein incorporated by reference. The transformed hairy roots can be grown using at least one soil amendment and pathogenicity tested and compared to that of control lines. To test candidate SCN resistance genes, a candidate gene is introduced into soybean tissue using an *A. rhizogenes* Ri plasmid. The resulting hairy roots are grown and tested according to the methods of the invention.

EXPERIMENTAL

The following examples are offered by way of illustration.

Example 1

Preparation of Soybean Root Sections

An example of the methods of the present invention in a hairy root assay using soybean (*Glycine max*) and SCN was performed to demonstrate the increased pathogenicity measures obtained through the use of a soil amendment.

In the experiment soybean seeds of a variety previously transformed with *Agrobacterium rhizogenes* to produce hairy roots and known to be susceptible to SCN were sterilized for 3 minutes in 50% (v/v) bleach (Ultra Clorox) and germinated on 1% agar plates in a growth chamber (26° C., 16 hr/8 hr of light/dark respectively). Roots from the germinated plants were dissected into pieces of approximately 5 cm and transferred into Petri dishes containing Gamborg's B5 medium (Sigma, St. Louis, Mo.) for inoculation.

Example 2

Preparation of SCN J2

*Heterodera glycines* (race 3) cysts were collected from infected soybean roots in the greenhouse. Eggs were collected on 25-μm-pore sieve after crushing the cysts to release the eggs. A 35% sucrose solution was used to separate eggs from silt and other debris by centrifugation at 350 g for 5 minutes. Cleaned eggs were sterilized in 10% (v/v) bleach solution for 3 minutes.

The sterilized eggs were placed on a nylon screen placed over a solution of 3.14 mM $ZnSO_4$ solution. The screen allowed contact with both the air and the solution. After 7 days, J2 stage SCN were collected, sterilized in 0.001% $HgCl_2$ for 3 minutes, and suspended in 1% low-gelling agarose (SeaPlaque® Agarose [0.8%]+SeaPrep® Agarose [0.2%])(Cambrex Corp., East Rutherford, N.J.) at a concentration of approximately 10 J2/μl.

Example 3

Root Infection and Growth

Each plate received 100 μl of the J2 solution. Plates were incubated in the dark at 26-28° C. for 7 weeks. Two treatment groups, each consisting of 24 plates, were used in this experiment. Plant type and SCN type were the same between treatment groups. The control group received no TURFACE® (calcined clay). After addition of the J2 solution, the TURFACE® (calcined clay) was added to the experimental group. Three grams of the TURFACE® (calcined clay) was added in a uniform layer over the entire surface of the plate. The TURFACE® (calcined clay) remained on the plate for the duration of the 7 week growth phase.

Example 4

Scoring Plates

Six to eight weeks after J2 inoculation, SCN cyst images were recorded from each plate using the method as described in Lu, et al., 2005; (Journal of Nematology 37(4):495-499). The image device consists of an enclosed lighting system (KL 2500 LCD, Leica, Solms, Germany), a camera (Spot RT, Diagnostic Instruments Inc., Sterling Heights, Mich.), and a computer (Pentium 4, Dell, Austin, Tex.). The high-sensitivity gray-scale camera is equipped with a zoom lens. A bandpass filter was placed before the lens to allow optimal wavelengths through to produce a high-contrast image. Halogen light was used as the excitation light source. To allow required light to excite the samples, another bandpass filter was placed on the excitation light path. The power of the light was carefully adjusted to give an adequate excitation without photobleaching of the sample. Guides were used to introduce the light to the sample. Cyst numbers on each plate were manually counted from the computer screen or JPEG images of all plates were automatically processed using a LemnaTech Daphnia software.

Example 5

Results

Figure 2:
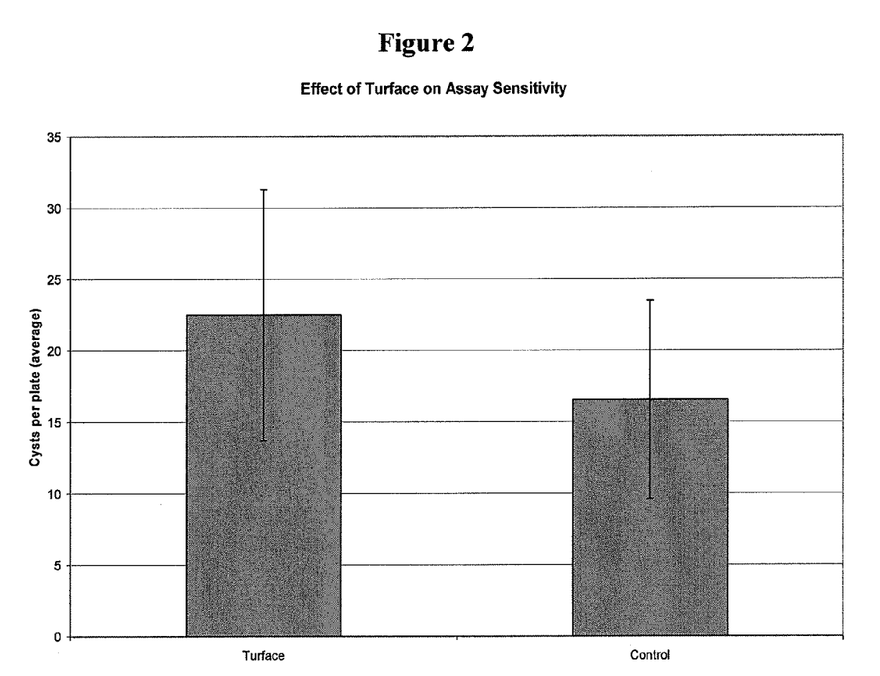
FIG. 2 is a graph depicting the results from hairy root assays for soybean cyst nematode conducted with and without the use of a soil amendment.

The experimental plates yielded an average of 22.5 cysts per plate with a standard deviation of 8.77, control plates yielded an average of 16.5 cysts per plate with a standard deviation of 6.93. FIG. 2 is a graph showing the results. Although the treatment group means were not statistically different, the highest number of cysts reported in the experimental group had several plates with over 30 cysts, something which was quite rare when the traditional assay (without a soil amendment) was performed.

Example 6

Effect of Adding Water to Soil Amendment

In order to determine what effect, if any, would result from adding water to the soil amendment before placing the soil amendment on the plate. As a result, another experiment was performed using similar conditions as above. Root sections were prepared and set into Petri plates according to Example 1, and SCN J2 were prepared according to Example 2.

Each plate received 100 µl of the J2 solution. Plates were incubated in the dark at 26-28° C. for 7 weeks. Plant type and SCN type were the same between treatment groups. Four treatment groups were used. Group one, consisting of 30 plates, received no TURFACE® (calcined clay) amendment, plants in group two, consisting of 6 plates, were covered with 3 grams of dry Turface® soil amendment, plants in group three, consisting of 7 plates, were covered with 3 grams moist (approximately 3 ml water per 3 g of TURFACE®) TURFACE® (calcined clay) soil amendment, plants in group four, consisting of 8 plates, were treated with 6 ml of wet (some visible water above the TURFACE® (calcined clay) and carried along with the TURFACE® (calcined clay) to the treatment) TURFACE® (calcined clay). Females and cysts were counted at 8 weeks after infection.

Plates were scored using the automated counting system set forth in Example 4.

Figure 3:
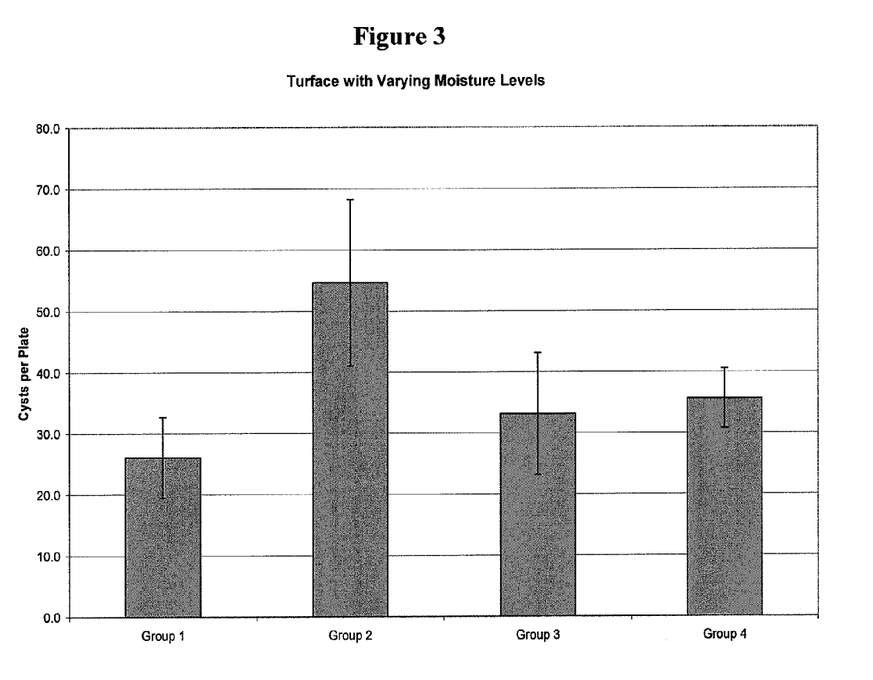
FIG. 3 is a graph depicting the results from hairy root assays where the assay of Group 1 was conducted without the use of a soil amendment and Groups 2-3 were conducted according to the methods of the present invention. Groups 2-3 had increasing amounts of water added to the soil amendment before the soil amendment was used in the assay.

FIG. 3 is a graphical representation of the average number of cysts counted in each treatment group. The group 1 averaged 26.1 cysts per plate with a standard deviation of 6.6 cysts. Group 2 demonstrated the greatest increase in the number of cysts per plate with 54.7 cysts per plate and a standard deviation of 13.6. Group 3 and 4 averages were statistically identical with an average of 33.1 and 35.6 cysts per plate respectively; standard deviations were 10.0 and 4.9 accordingly. Group 4 was statistically higher than group 1 without TURFACE® (calcined clay). Group 3 was higher than group 1, despite the fact that the means were not statistically different, group 3 showed consistently higher scores than group 1.

The results show that the addition of a soil amendment, such as TURFACE® (calcined clay), does not decrease and generally results in an increase in the number of SCN counted.

Additionally, the results show that better results are obtained when no water is added to the soil amendment before use.

Example 7

Testing of Different Soybean Lines to Show Method Sensitivity

In order to demonstrate the sensitivity of the methods of the present invention five different soybean lines of varying susceptibility were used in a hairy root assay with SCN.

In the experiment soybean seeds of 5 cultivars previously transformed with *Agrobacterium* to produce hairy roots were used. 93B82 was susceptible to SCN while 93B15 was moderately susceptible to SCN. 95M50 was moderately resistant to SCN and 92B12 and 92M75 were resistant to SCN. Root sections from each cultivar were prepared and set into Petri plates according to Example 1, and SCN J2 were prepared according to Example 2. Each plate received 100 µl of the J2 solution. Plates were incubated in the dark at 26-28° C. for 7 weeks. Five treatment groups based on plant type, each consisting of 24 plates, were used in this experiment. SCN type was constant between treatment groups. After addition the J2 solution, 3 grams of dry (no moisture added) TURFACE® (calcined clay) was added to each plate. The TURFACE® (calcined clay) was added in a unifonu layer over the entire surface of the plate. The TURFACE® (calcined clay) remained on the plate for the duration of the 7 week growth phase. Plates were scored using the automated counting system set forth in Example 4.

Figure 4:
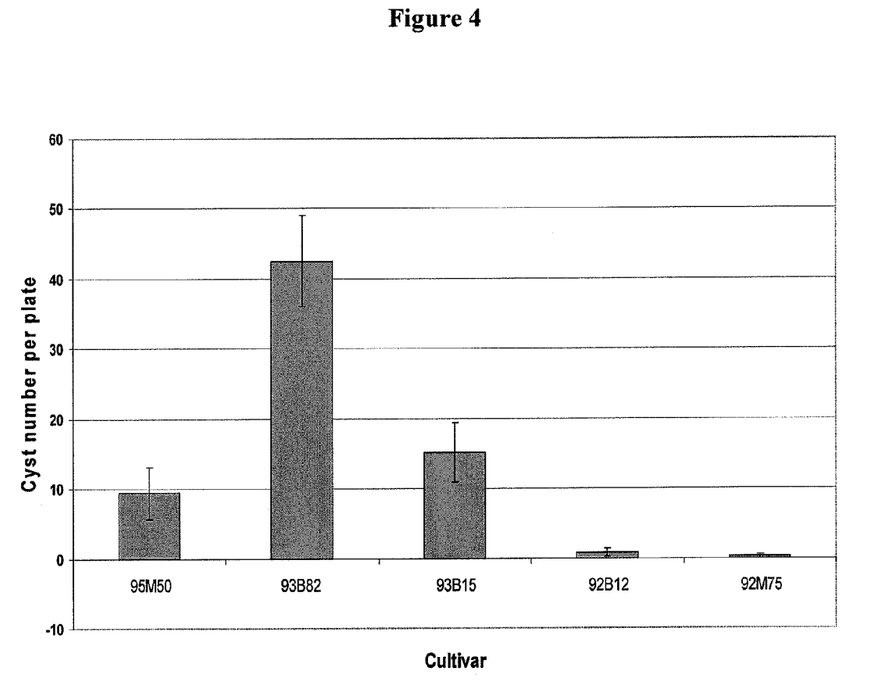
FIG. 4 is a graph depicting the results from hairy root assays conducted on plants exhibiting varying degrees of tolerance to SCN. 93B82 was susceptible to SCN while 93B15 was moderately susceptible to SCN. 95M50 was moderately resistant to SCN and 92B12 and 92M75 were resistant to SCN.

FIG. 4 is a graphical representation showing the average number of cysts per plate in each treatment group. The average number of cysts per plate for susceptible cultivar 93B82 (S) was 42.82 with a standard deviation of 6.3. The average number of cysts per plate for moderately susceptible cultivar 93B15 (MS) was 14.52 with a standard deviation of 4.1. This was statistically different from every group except moderately resistant cultivar 95M50 (MR) which had an average of 9.59 cysts per plate with a standard deviation of 3.6. Resistant cultivars 92B12 and 92M75 had 0.8 and 0.2 cysts per plate with a standard deviation of 0.6 and 0.3 respectively. The averages of groups 4 and 5 did not differ significantly from each other but did differ significantly from the other groups.

The results show the increased sensitivity produced using methods of the present invention. There was a clear, statistically significant difference between susceptible and tolerant groups. Additionally, the results observed generally mirror results which would be expected using traditional greenhouse testing methods. T. Niblack et al., *A Standard Greenhouse Method for Assessing Soybean Cyst Nematode Resistance in Soybean: SCE*08, Plant Health Progress, May 13, 2009. These results demonstrate that the methods of the present invention may be used to improve sensitivity allowing for better discrimination between lines exhibiting different levels of tolerance to a plant root pathogen.

A method for improving the sensitivity of assays for plant root pathogens has been disclosed. The method may be used to improve the sensitivity of assays for any kind of plant including monocots and dicots. Examples of plants which may be used in the methods of the present invention include maize, wheat, rice, millet, barley, sorghum, alfalfa, oilseed Brassica, cotton, sunflower, potato or tomato. Any plant root pathogen may be used in the methods of the present invention including nematodes which include soybean cyst nematodes and root-knot nematodes. A wide variety of soil amendments may be used in the methods of the invention including sand, cat litter, oil absorbents, grease absorbents, calcined diatomaceous earth, crushed aggregates, and calcined clay. The calcined clay used with the invention may be a smectite clay including beidellite, nontronite, nectorite, saponite, attapulgite or sepulite. The smectite clay may include both montmorillinite and opal CT. The methods of the present invention result in a better measure of the pathogenicity of the studied plant root pathogen. This measure may be used to determine a plant's resistance to the pathogen and the pathogenicity of the pathogen. Additionally, the improved measure of pathogenicity may be used as part of a plant breeding program to develop plants which are better able to tolerate the plant root pathogen in the field.

Throughout the specification examples have been used to illustrate the present invention. It is to be understood that the present invention contemplates numerous variations, modifications, and alternatives. As such, the scope of the claims should not be limited by the various examples provided herein.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method of evaluating a plant for resistance to a plant root pathogen comprising:
   a) exposing a dissected portion of a root of a plant to a pathogen, wherein the dissected portion of the root of the plant is on a root culturing substrate at least partially covered by a soil amendment selected from: cat litter, oil absorbents, grease absorbents, calcined diatomaceous earth, crushed aggregates, and calcined clay for a period of time; and
   b) measuring the plant's resistance to the plant root pathogen.

2. The method of claim 1 where the plant is maize, wheat, rice, millet, barley, sorghum, rye, soybean, alfalfa, oilseed Brassica, cotton, sunflower, potato or tomato.

3. The method of claim 1 where the pathogen is a nematode.

4. The method of claim 3 where the nematode is selected from the group consisting of soybean cyst nematode and root knot nematode.

5. The method of claim 1 where the calcined clay is a smectite clay.

6. The method of claim 5 where the smectite clay is beidellite, nontronite, hectorite, saponite, attapulgite or sepiolite.

7. The method of claim 1 where the calcined clay further comprises montmorillinite and opal CT.

8. The method of claim 1 where the step of measuring the plant's resistance to the pathogen further comprises counting the number of individuals of the pathogen on a dissected portion of the root.

9. The method of claim 1 where the step of measuring the plant's resistance to the pathogen further comprises weighing the dissected portion of the root.

* * * * *